United States Patent [19]
Chassaing

[11] 3,957,035
[45] May 18, 1976

[54] OPHTHALMOLOGICAL DEVICE USEFUL FOR EYE SURGERY

[76] Inventor: Jean Chassaing, 23, avenue de la Gare, Brive, Correze, France

[22] Filed: Jan. 17, 1975

[21] Appl. No.: 541,766

Related U.S. Application Data

[63] Continuation of Ser. No. 380,586, July 19, 1973, abandoned.

[30] Foreign Application Priority Data

Sept. 8, 1972 France .............................. 72.31840

[52] U.S. Cl. ............................. 128/2 T; 128/303 R
[51] Int. Cl.² ............................................. A61B 3/00
[58] Field of Search ......... 128/2 T, 2 R, 303, 303.1, 128/303.11; 351/6, 7

[56] References Cited
UNITED STATES PATENTS

| | | | |
|---|---|---|---|
| 2,780,221 | 2/1957 | Posner | 128/2 T |
| 2,811,969 | 11/1957 | Shubert | 128/303 R |
| 3,519,338 | 7/1970 | Papritz | 351/7 |
| 3,598,478 | 8/1971 | Townsley | 351/6 |
| 3,706,304 | 12/1972 | Sisler | 128/2 T |
| 3,736,938 | 6/1973 | Evvaro et al. | 128/2 T |

FOREIGN PATENTS OR APPLICATIONS

| | | | |
|---|---|---|---|
| 135,577 | 1/1960 | U.S.S.R. | 128/2 T |
| 724,486 | 1/1932 | France | 128/303 |

Primary Examiner—Kyle L. Howell
Attorney, Agent, or Firm—Young & Thompson

[57] ABSTRACT

A device for ophthalmological examination and treatment of the fundus of the eye comprises a fitting removably mounted on an ophthalmoscope and a probe which is carried by the fitting. The probe has a curved free end which can be passed around the patient's eyeball within the orbit and intercepts the sighting axis of the ophthalmoscope. The other end of the probe is mounted on the fitting in such a manner as to permit longitudinal and rotational displacement with respect to the sighting axis.

7 Claims, 6 Drawing Figures

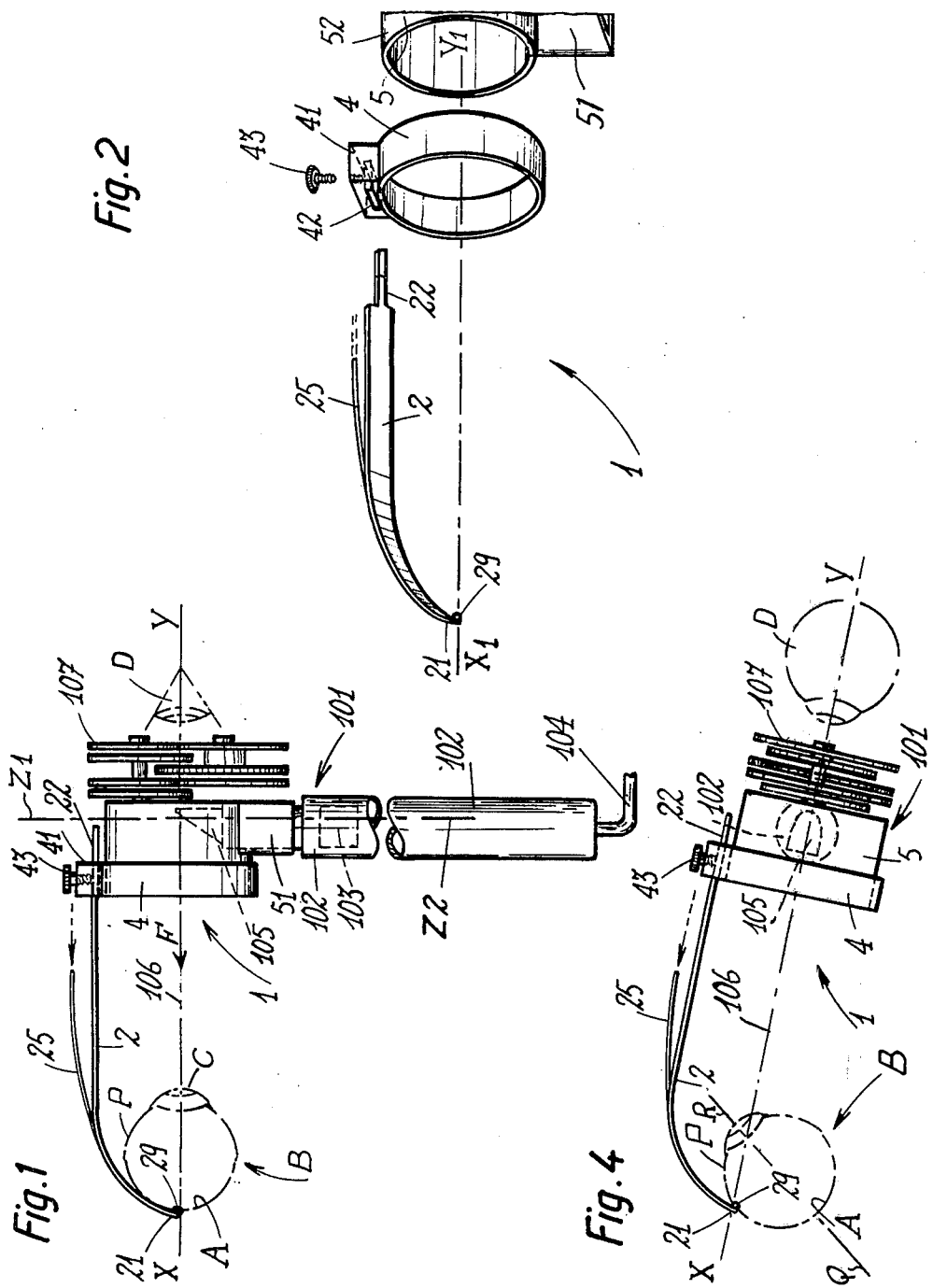

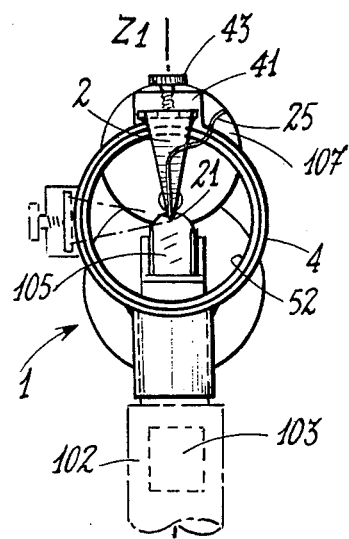
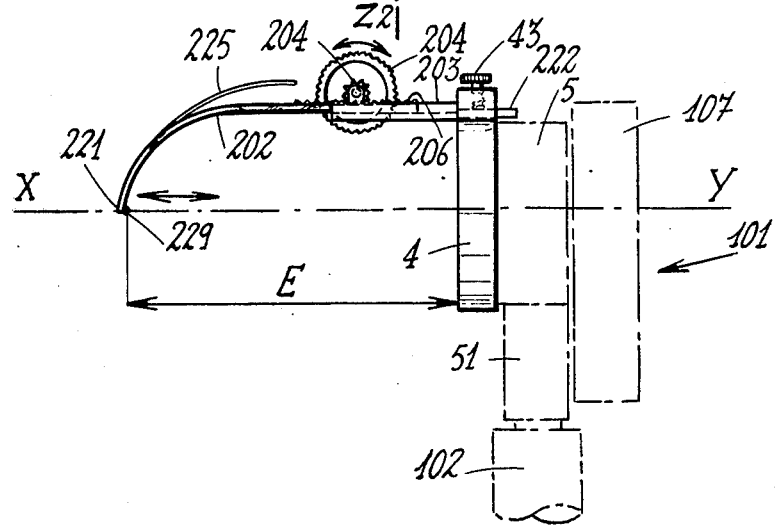
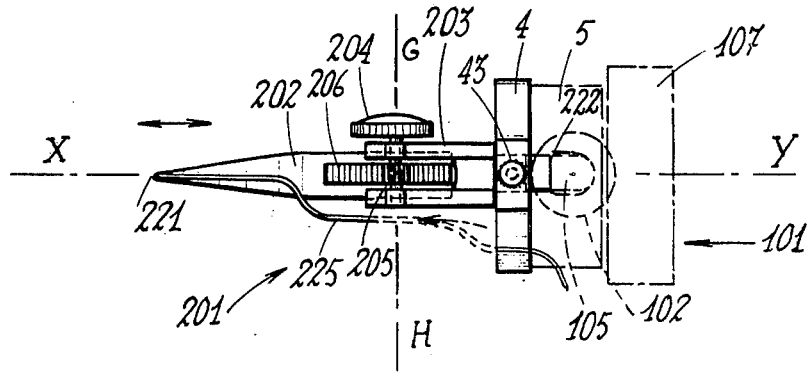

OPHTHALMOLOGICAL DEVICE USEFUL FOR EYE SURGERY

This application is a continuation of application Ser. No. 380,586, filed July 19, 1973, now abandoned.

A well-known optical apparatus for inspecting the fundus of the eyes of patients is the ophthalmoscope which basically comprises a light source associated with an optical system for producing a narrow beam of light which the practitioner directs through the eye onto the portion of fundus to be examined, while observing this illuminated portion through a sighting aperture whose axis coincides with that of the light-beam-producing optical system. Once the inspection by means of the ophthalmoscope is completed, the practitioner operates on any lesion which has been discovered, through the adjacent portion of the sclera, i.e. from the back of the eyeball, and therefore has a serious problem of accurately locating the lesion inasmuch as the latter which was visible in the ophthalmoscope during inspection, is no longer visible from the back of the eyeball during operation.

This problem is alleviated by the use of so-called "localizers" which are small instruments inserted against the eyeball within its orbit and designed to make a locating mark on the sclera. To this end, the practitioner first endeavors to place his localizer in posterior contact with the lesion of the fundus while controlling this superposition by means of the ophthalmoscope. When coincidence has been achieved the localizer leaves a mark which may be either mechanical or diathermic.

One known instrument for this purpose is a scleral probe consisting of an elbowed pin with a handle which serves to apply pressure on the sclera and to form an internal projection which is visible through the ophthalmoscope. The pin leaves a mark on the sclera and this localizes the point of pressure. However, this device has various limitations, as regards for example accuracy.

Another known type of localizer with electrical illumination produces a luminous spot which is visible by translucency through the eye wall and carries a diathermic electrode which leaves a mark on the sclera. However, it is a fairly difficult matter to place the luminous spot at the correct location with the desirable degree of precision since the light beam of the ophthalmoscope tends to cause the spot to disappear by reducing the effect of contrast.

All these instruments are subject to the following disadvantage : it is not always easy for the practitioner, especially under certain circumstances such as ocular media having low transparency or a marked degree of retinal detachment, to bring the localizer against the sclera in precise and constant coincidence with the spot formed on the retina by the light beam of the ophthalmoscope. Under these conditions, the accuracy and rapidity of the treatment are often unsatisfactory. The same applies to indirect binocular ophthalmoscopy in which it is necessary, for example, to place a cryode in postion behind the lesion and under visual control with a view to subjecting said lesion to low-temperature treatment.

An object of the present invention is to overcome these drawbacks and limitations, and enable the practitioner to attain easily, quickly and with pinpoint accuracy the proper location of a lesion on the patient's eye.

Another object of this invention is to provide a device which will automatically and safely combine simultaneous visual inspection and operative location of a lesion of the fundus of the eye.

A further object of this invention is to provide an accessory probe designed to supplement an ophthalmoscope by being fitted thereto and presenting a free end which is the free end of said probe being curved in order to pass round the patient's eyeball and to intercept the sighting axis aforesaid of the ophthalmoscope.

The combination of elements which characterizes this invention enables a practitioner to introduce the probe behind the eye wall either by exposing said wall or without modification of the tissues. Thus, the practitioner introduces the probe into the conjunctival sac, without opening the conjunctiva the probe being operated by means of the handle of the ophthalmoscope. Moreover, the invention provides the practitioner with a guarantee that the end of the probe which is introduced behind the eye wall continuously and accurately coincides with the point being sighted through the ophthalmoscope.

In a preferred embodiment of the invention, the probe is rotatably mounted on an axis which coincides with the sighting axis of the opthalmoscope. In another preferred arrangement, that extremity of the probe which is located on the sighting axis is placed at an adjustable distance with respect to the ophthalmoscope and is provided with therapeutic means for operating through the eye wall and also through the conjunctiva, the tissues and the eye wall, particularly by low-temperature treatment. These therapeutic means comprise a virtually punctual point-like active element located substantially on the sighting axis of the ophthalmoscope in any position of the probe and adapted to come into contact with the eye wall.

The rotation of the probe facilitates positioning of this latter on each meridian of the eyeball behind the sclera. The longitudinal adjustment facilitates examination of the retinal surface, and placing of the extremity of the probe in contact with the sclera. Interchangeability of the probe and the means carried at the end of this latter facilitate the operations involved in localization and treatment.

Further properties and advantages of the invention will become apparent from the following description of embodiments of the invention which are given by way of example without any limitation being implied, reference being made to the accompanying drawings, wherein :

FIG. 1 is a side view of the instrument according to the invention in the position of operation on the eyeball;

FIG. 2 is an exploded view in perspective showing the elements of the instrument of FIG. 1;

FIG. 3 is a front view of the front portion of the instrument of FIG. 1;

FIG. 4 is a top view of the localization instrument placed on a point of the retina which is anterior to the ocular equaton;

FIGS. 5 and 6 represent an alternative embodiment of the instrument shown in FIG. 1.

FIGS. 1 to 4 illustrate the invention as applied to a conventional ophthalmoscope 101, there being shown at 102 the ophthalmoscope handle containing a light source 103 which is supplied with electric current through a lead-wire 104.

The light source 103 emits a narrow light beam having an axis $Z_2-Z_1$ which coincides substantially with the axis of the handle 102. An optical system 105 of the prism type reflects the beam 106 in the direction of the arrow F along an axis x–Y which constitutes the sighting axis of the ophthalmoscope 101. This light beam could be of greater width but the axis of the beam would in that case be materialized by the image of a cross projected at the center of the luminous spot which illuminates the retina.

Provision is made on the opposite side with respect to the direction of the arrow F for an eyepiece composed of a system of lenses 107 having different magnifications which the practitioner can cause to coincide with the sighting axis X–Y in order to observe the fundus A of the patient's eye B through the pupil C.

To this end, the practitioner places his eye D on the sighting axis (FIG. 1) and orients the light beam 106 by means of the handle 102 in order to scan the fundus of the eye A and to hold the luminous spot if necessary on any particular portion which is to be observed in greater detail.

In accordance with a preferred embodiment of the invention (shown in FIGS. 1 and 2), the instrument 1 comprises a fitting 5 which is adapted to be attached to the above described conventional ophthalmoscope 101. The fitting 5 is provided with an elastic fastening element 51 which is intended to fit steadily over the upper portion of the casing of the ophthalmoscope 101 in order that the axis $X_1-y_1$ of a sleeve 52 carried by the fitting 5 may be caused to coincide by design with the sighting axis X–Y of the ophthalmoscope 101.

A mounting-collar 4 provided with an external boss 41 is fitted with slight friction on the sleeve 52. There is formed in said boss a groove 42 which is directed parallel to the axis X–Y and into which opens an internally threaded bore for a clamping-screw 43. The rear end 22 of a curved probe 2 is mounted within the groove 42. The screw 43 serves to lock the probe 2 in position with respect to the mounting-collar 4, the rear end 22 of probe 2 being engaged to a greater or lesser extent within the groove 42 which performs the function of an adjusting guide.

At its other end, i.e. opposite to the above attachment end 22, the probe 2 is curved to pass around the eyeball B and its tip 21 which is meant to engage the sclera P is positively positioned on the sighting axis X–Y of the ophthalmoscope 101.

The probe 2, the collar 4 and the fitting 5 can be of metal such as brass or stainless steel or even of molded plastic material.

By virtue of the arrangement which has just been described, the mounting-collar 4 which carries the curved probe 2 can be rotated by hand about the sighting axis X–Y of the ophthalmoscope 101. The tip 21 which is located on said axis by design therefore continues to intercept this axis X–Y if the probe is rotated about said axis.

A tube 25 of metal or plastic material is attached to the probe 2 and leads to its tip 21. This tube 25 is intended to be connected to a number of different auxiliary means (not shown in the drawings) which are carried by the handle 102 of the ophthalmoscope 101, depending on the nature of the functions to be performed by the probe 2. Said probe is removable and interchangeable, with the result that a set of probes 2 can be employed in turn; the tip 21 of each probe is provided with point-like active element 29 which is subjected to the action of the auxiliary means aforesaid by means of the tube 25 as has just been mentioned. Thus, the point-like active element 29 can be fitted, for example, with electric heating means (diathermy) or a galvanic tip or means for cryogenic treatment supplied by a circulation of fluid at low temperature or else means for mechanical and chemical marking (carbon). The use of these latter can be particularly advantageous in the case of visible foreign bodies which are fixed on the retina.

In order to examine the fundus A of eye B by means of the ophthalmoscope 101 (shown in FIG. 1) as mentioned in the foregoing, the practitioner holds the handle 102 in a substantially vertical position and places his eye D on the sightng axis X–Y at the end remote from the probe 2. Provision is made for a system of lenses 107 having a number of different magnifications. By means of the rotating assembly of the probe 2, it is only necessary to cause the mounting-collar 4 to rotate about the axis X–Y in order to place the probe 2 exactly in the ocular meridian which corresponds to a particular retinal lesion.

In order to move the probe 2 around the eyeball B, the practitioner can cause the pivotal displacement of the ophthalmoscope handle which carries the entire device. For the sake of convenience of examination, the practitioner can also produce action progressively on the boss 41 of the mounting-collar 4 in order to cause this latter to rotate on the sleeve 52 of its fitting 5 and finally to bring the probe 2 into the most suitable position of operation. During these movements, the element 29 remains continuosly located on the sighting axis X–Y since the collar 4 is designed to rotate about said axis.

By pulling backwards the ophthalmoscope to a slight extent, the practitioner can apply the element 29 against the sclera and produce action through the wall P by any of the therapeutic means which have already been mentioned in connection with the point-like active element 29 placed on the tip 21 and supplied or controlled by means of the tube 25.

The continuous coincidence of the element 29 with the sighting axis X–Y enables the practitioner to operate in complete safety and without any delay on the desired point which has been sighted by him on the fundus A of the eye B. As has been seen, the invention in fact ensures continuous and accurate superposition of the point which is sighted optically on the inside of sclera P and of the probe tip 21 which engages the outside of sclera P.

In one advantageous alternative embodiment of the invention (as shown in FIGS. 5 and 6); the mounting-collar 4 carries a guide 203 having an axis parallel to the rotational and sighting axis X–Y. The guide 203 is mounted on the ring by means of its end-portion 222 which is similar to the extremity 22 of the probe 2 shown in FIG. 2. The guide 203 is provided with a knurled adjusting-wheel 204 (shown in FIG. 6) which is associated with a pinion 205 mounted along a transverse axis G–H with respect to the axis X–Y. A probe 202 is so arranged as to slide within the guide 203 whilst a rack 206 carried by the probe 202 is disposed in meshing engagement with the pinion 205.

By means of this device, the practitioner can readily modify the distance E from the of the probe 202 mounting-collar 4 by rotating the knurled wheel 204 without interfering with the sighting (as shown in FIG. 5).

I claim:

1. An ophthalmological device useful for eye surgery, comprising in combination:

an ophthalmoscope having (i) an optical system for projecting a beam of light along a sighting axis onto the fundus of a patient's eye in order to illuminate a inside point of the fundus lying on said axis, and (ii) an eyepiece for taking a sight on said illuminated inside point, and a probe having (i) an attachment end portion connected to and protruding from said ophthalmoscope opposite to said eyepiece thereof at a distance from said sighting axis, and (ii) a curved free end portion that curves towards said sighting axis and terminates in a point-like operative tip which lies on said sighting axis to pass around the patient's eyeball and engage an outside point of the sclera in registry with said illuminated inside point of the fundus.

2. An ophthalmological device according to claim 1, further comprising means for translationally fitting said probe on said ophthalmoscope parallel to said sighting axis, and means for adjusting the position of said probe to control the distance between said operative tip thereof and said ophthalmoscope.

3. An ophthalmological device according to claim 1, further comprising means for rotatingly fitting said probe on said ophthalmoscope about said sightng axis, and means for adjusting the angular position of said probe with respect to said ophthalmoscope.

4. An ophthalmological device according to claim 3, wherein said rotatingly fitting means comprise a collar on which said attachment end portion of the probe is mounted, said collar being rotatable on and with respect to the ophthalmoscope about said sightng axis.

5. An ophthalmological device according to claim 4, further comprising a cylindrical sleeve mounted on the ophthalmoscope and presenting an axis which coincides with said sighting axis, said sleeve supporting said collar.

6. An ophthalmological device according to claim 4, wherein the probe is attached to the collar by means of a guide substantially parallel to said sighting axis.

7. An ophthalmological device according to claim 6, further comprising locking means for temporarily locking the probe with respect to the guide.

* * * * *